(12) United States Patent
Divo et al.

(10) Patent No.: US 6,643,994 B1
(45) Date of Patent: Nov. 11, 2003

(54) PROCESS FOR CONVERTING A CONTINUOUS STRUCTURE INTO DISCRETE, SPACED APART ELEMENTS

(75) Inventors: Michael Divo, Friedrichsdorf (DE); Ludwig Busam, Hunstetten (DE); Christofer Fuchs, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/744,276

(22) PCT Filed: Jul. 16, 1999

(86) PCT No.: PCT/US99/16139

§ 371 (c)(1),
(2), (4) Date: Jan. 22, 2001

(87) PCT Pub. No.: WO00/04856

PCT Pub. Date: Feb. 3, 2000

(30) Foreign Application Priority Data

Jul. 22, 1998 (EP) ............................................. 98113666

(51) Int. Cl.$^7$ ................................................ A61F 13/15
(52) U.S. Cl. ........................... 53/450; 53/435; 53/444; 493/210; 493/227; 493/235; 493/236
(58) Field of Search .......................... 53/435, 444, 450; 493/210, 227, 235, 236

(56) References Cited

U.S. PATENT DOCUMENTS

| | | | | |
|---|---|---|---|---|
| 3,916,597 A | * | 11/1975 | Martelli ........................ | 53/415 |
| 4,517,714 A | * | 5/1985 | Sneed et al. .................. | 28/103 |
| 4,904,440 A | | 2/1990 | Angstadt | |
| 5,237,800 A | * | 8/1993 | Omori ......................... | 53/433 |
| 5,458,592 A | | 10/1995 | Abuto et al. | |
| 5,691,035 A | | 11/1997 | Chappell et al. | |
| 6,115,997 A | * | 9/2000 | Burrow et al. ................ | 53/412 |
| 6,173,554 B1 | * | 1/2001 | Marbler ....................... | 53/412 |

FOREIGN PATENT DOCUMENTS

| | | |
|---|---|---|
| EP | 0 556 749 A | 8/1993 |
| EP | 0 650 714 A1 | 5/1995 |

* cited by examiner

*Primary Examiner*—Rinaldi I. Rada
*Assistant Examiner*—Brian D Nash
(74) *Attorney, Agent, or Firm*—Michael P. Hayden; Ken K. Patel

(57) ABSTRACT

The present invention relates to a process for converting a continuous structure into discrete, spaced apart elements by means of an expandable support web. First, the continuous structure is combined with a support web comprising longitudinal expansion means. Then, after separation of the continuous structure into discrete elements, the discrete elements are spaced apart by expanding the support web. The process of the present invention is particularly well suited for the industrial manufacture of articles comprising fragile discrete elements supplied to the production process in continuous form.

15 Claims, No Drawings

PROCESS FOR CONVERTING A CONTINUOUS STRUCTURE INTO DISCRETE, SPACED APART ELEMENTS

FIELD OF THE INVENTION

The present invention relates to a process for converting a continuous structure into discrete, spaced apart elements. Such a process is applicable in the industrial manufacture of discrete articles which are assembled from raw materials supplied in continuous form.

BACKGROUND

Generally, the industrial manufacture of discrete articles relies on the assembly of individual articles from continuously supplied raw materials. Continuously supplied raw materials can be supplied to the manufacturing process in a much more convenient way than discrete raw materials. The continuously supplied raw materials are cut to obtain discrete elements which are then deployed in the articles. Often, it is desirable to space apart the elements in the machine direction to improve the processability of the elements, e.g. in the context of enveloping or packaging.

In many cases, articles comprise fragile elements which are combined with, for example, a protective layer or a packaging layer. These additional layers can provide support to the fragile elements to avoid disintegration of the elements by external forces encountered during transport, storage, and use.

When the raw material for such fragile elements is supplied to the making process in form of a continuous structure, the conversion of the continuous structure into discrete, spaced apart elements such that they can subsequently be covered or wrapped requires a lot of effort and caution on the process side. In particular, spacing apart the fragile elements as such requires a pull force which is potentially harmful to the integrity of the discrete elements. Secondly, reducing the pull force for improved element handling requires the reduction of the line speed.

One example of discrete articles comprising fragile elements are disposable absorbent articles. Typically, an absorbent core comprised in such disposable absorbent articles is based at least partially on a cellulosic fibrous matrix wherein the integrity of the absorbent core often relies on the entanglement of the individual fibers. In addition, disposable absorbent articles generally comprise a topsheet and backsheet between which the absorbent core is sandwiched. By joining topsheet and backsheet at least along the periphery of the absorbent core, the disintegration of the fragile absorbent core is reduced. Some disposable absorbent articles even comprise additional wrapping layers around the absorbent core to further reduce disintegration of the absorbent core.

Specifically, U.S. Pat. No. 5,458,592 issued to Abuto et al. teaches an absorbent core completely wrapped in a thermoplastic fibrous nonwoven web. The process for making these absorbent structures as described in this patent is limited to the formation of discrete, spaced apart absorbent cores. This specific formation allows the subsequent wrapping of the cores without needing to space apart the fragile absorbent cores before wrapping them.

On the other hand, continuous absorbent core formation processes, as described for example in U.S. Pat. No. 4,904,440 issued to Angstadt, have the need that the continuous web of absorbent cores has to be cut into discrete cores and subsequently these discrete cores have to be spaced apart before they can be combined with another continuous web (such as a core wrap, topsheet, backsheet, or the like) at spaced apart positions. Especially in the context of fragile absorbent cores, these operations on the discrete absorbent cores cause line speed limitations, increased process complexity and maintenance effort.

Hence, it is an objective of the present invention to provide a process for converting a continuous structure into discrete, spaced apart elements without imposing the above limitations.

Therefore, the process of the present invention is particularly well suited for the manufacture of discrete articles comprising fragile absorbent cores.

SUMMARY OF THE INVENTION

It is an object of the present invention to provide a process for converting a continuous structure into discrete, spaced apart elements, comprising the steps of (a) supplying a continuous support web which is combined with the continuous structure, the support web comprising at least one longitudinal expansion means; (b) separating the continuous structure into discrete elements; and (c) longitudinally spacing apart the discrete elements by expanding the support web. Thereby, the support web preferably comprises at least one deactivatable expansion obstruction means. In a preferred embodiment of the process of the present invention, the step of deactivating the deactivatable expansion obstruction means of the support web is comprised in the process. Alternatively, the support web may be a discontinuously expanding web.

It is a further object of the present invention to provide a process which comprises a step of introducing designated transverse separation zones into the continuous structure.

It is a further object of the present invention to provide a process for converting a continuous structure into discrete, spaced apart elements wherein the step of expanding the support web is carried out by a series of two consecutive conveyors transporting the support web, the second conveyor having a higher transportation velocity than the first conveyor.

It is a further object of the present invention to provide a process for converting a continuous structure into discrete, spaced apart elements which comprises the step of forming the continuous structure of core elements and the step of transferring the continuous structure onto the support web.

It is a further object of the present invention to provide a process for converting a continuous structure into discrete, spaced apart elements which comprises the step of forming the continuous structure on the support web.

It is a further object of the present invention to provide a process for converting a continuous structure into discrete, spaced apart elements wherein the elements are absorbent cores.

It is a further object of the present invention to provide a process for making discrete articles comprising at least one discrete element and a support web, wherein the process comprising the steps of converting a continuous structure into discrete, spaced apart elements and the step of separating the continuous support web between at least some the discrete elements.

It is a further object of the present invention to provide a process for making discrete articles which comprises the step of folding the support web around at least one longitudinal or at least one transverse edge of the discrete elements.

It is a further object of the present invention to provide a process for making discrete articles further comprising the step of longitudinally wrapping the support web around the discrete elements such that the longitudinal edges of the support web overlap and the step of completely enveloping the discrete elements by sealing the support web along the overlapping longitudinal edges of the support web and by sealing the support web outside the transverse edges of the discrete elements.

It is a further object of the present invention to provide a process for making discrete articles which comprises the step of supplying a second support web and the step of positioning the discrete elements intermediate the support web and the second support web.

It is a further object of the present invention to provide a process for making discrete articles which comprises the step of completely enveloping the discrete elements by attaching the support web to the second support web outside the longitudinal and transverse edges of the discrete elements.

It is a further object of the present invention to provide a process for making discrete articles wherein the articles are absorbent articles.

DETAILED DESCRIPTION OF THE INVENTION

The present invention relates to a manufacturing process for converting a continuous structure into discrete, spaced apart elements.

Any element that can be supplied to the process in form of a continuous structure is suitable for being converted by the process of the present invention. A suitable continuous structure can either be elastic or non-elastic.

In one embodiment of the process of the current invention, the continuous structure is made off-line (i.e. preformed) and subsequently supplied to the process in continuous form, for example as roll stock. In another embodiment of the process of the present invention, the continuous structure is made online, for example by physical or chemical transformation of one or more raw materials into a continuous structure. The term "online" as used herein describes a process step which is comprised in the same process as the essential steps of the process of the present invention. The term "offline" as used herein describes a process step which is separate from the process of the present invention.

The process of the present invention is particularly suitable for elements that have only low tensile strength, i.e. already low external forces exerted on the element cause reduced usability of the element by disintegrating or deforming it. Particular examples of such elements having low tensile strength are conventional absorbent cores comprised in absorbent articles.

Optionally, the continuous structure converted in the process of the present invention may comprise designated separation zones. These designated separation zones are designed to allow easy separation of the elements at their respective positions. For example, these zones may be characterized by a reduced basis weight compared to the remaining part of the continuous structure. Alternatively, these zones may be characterized by side notches to effectively reduce the width of the continuous structure at the designated separation zones or by a partial, vertical cut through the continuous structure to reduce the separation tension of the continuous structure.

According to the present invention, the continuous structure is combined with a support web.

In one embodiment of the process of the present invention, the support web is supplied to the process in continuous form, such as roll stock. In another embodiment of the process of the present invention, the continuous support web is made online, for example by forming a nonwoven web by techniques well known in the art. In another embodiment of the process of the present invention, the continuous structure is pre-combined with the support web and the combined structure is supplied to the process as a whole.

To be suitable for the process of the present invention, the support web comprises longitudinal expansion means. Preferably, the longitudinal expansion means are positioned at regularly spaced intervals within the support web. More preferably, the support web additionally comprises deactivatable expansion obstruction means accompanying the longitudinal expansion means. The longitudinal expansion means as well as the deactivatable expansion obstruction means may be already comprised in the support web when it is supplied to the process of the present invention or they may be incorporated into the support web as part of the process of the present invention.

The term "web material" as used herein refers to a sheet-like material, or to a sheet-like composite or to a laminate comprising two or more sheet-like materials or composites. Typically, such a web material comprises a longitudinal dimension and a transverse dimension substantially smaller than the longitudinal dimension and it has a caliper also substantially smaller than its longitudinal dimension. For example, a web material can be a fibrous web, a non-fibrous web, a foam, or the like. The term "longitudinal expansion means" as used herein refers to a means that allows the web material to expand in longitudinal direction by a predetermined amount. After this expansion, the web material preferably exhibits a behavior under longitudinal tension similar to a conventional web material. The term "deactivatable expansion obstruction means" as used herein refers to a means that is preventing the expansion of a web material comprising a longitudinal expansion means. Furthermore, the deactivatable expansion obstruction means is designed such that it can be deactivated by an external deactivation device. After deactivation of the deactivatable expansion obstruction means the longitudinal expansion means can be utilized to longitudinally expand the web material at the position of the respective longitudinal expansion means.

Suitable web materials comprising longitudinal expansion means and deactivatable expansion obstruction means are described in European patent application No. 98108122.7. Preferably, the support webs used in the process of the present invention have a Relative Elastic Modulus Reduction of at least 50%, even more preferably at least 75%, most preferably at least 90% when submitted to the Deactivated Expansion Obstruction Test described herein.

Alternatively, the support web may be a discontinuously expandable web material as described in EPO patent application 98108123.5. Discontinuously expandable web materials have at least one longitudinal expansion means and are characterized in that the Relative Expansion Tension Reduction is at least 50%, preferably at least 75%, even more preferably at least 90% when such a web material is submitted to the Discontinuous Expansion Test described herein.

Exemplary types of a support web suitable for the current invention are a fibrous web, such as a tissue web, a nonwoven web, a woven web, a knit web, or the like. Such fibrous webs can be made from natural fibers (e.g., wood or cotton fibers), synthetic fibers (e.g., polyester or polypropylene fibers), or a combination of natural and synthetic fibers. A suitable non-woven support web may be by but is not limited to spunlace, spunbond, meltblown, carded, and/or air-through or calendar bonded. A suitable fibrous web may be absorbent or non-absorbent, liquid pervious, or liquid impervious.

Another embodiment of a support web suitable for the present invention is non-fibrous web such as a film. Such non-fibrous support webs may comprise polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE™ available from Dow Chemical Company and Exxact™ available from Exxon), and breathable polymers. A suitable film may also be co-extruded.

The non-fibrous support web may also be comprised of an apertured film, macroscopically expanded three-dimensional formed film, absorbent or foam, filled composition, or laminates and/or combinations therewith.

Suitable support webs of the present invention also include laminates of the above mentioned materials. Laminates may be combined by any number of bonding methods known to those skilled in the art. Such bonding methods include but are not limited to thermal bonding, adhesive bonding (using any of the number of adhesives including but not limited to spray adhesives, hot melt adhesives, latex based adhesives and the like), sonic bonding and extrusion laminating whereby a polymeric film is cast directly onto a substrate, and while still in a partially molten state, bonds to one side of the substrate, or by depositing meltblown fibers non-woven directly onto a substrate.

Alternatively, a support web suitable for the present invention may also comprise discretely distributed substances which are attached to the support web.

A preferred embodiment of a support web suitable for the present invention comprising longitudinal expansion means is obtained by arranging a conventional precursor web material in a transverse z-fold. The term "transverse z-fold" as used herein refers to two transverse folds which are arranged such that the longitudinal cross section of the web material looks like the letter "z" when looked at from the side. The z-fold allows the support web to comprise longitudinal expansion means without losing its essentially one or two dimensional configuration.

Another embodiment of the longitudinal expansion means suitable for the present invention is a plurality of transverse folds with alternating folding direction which are in close proximity to each other, called accordion fold hereafter.

Other suitable embodiments of the longitudinal expansion means suitable for the process of the present invention are regions of the web material which are mechanically strained, creped, corrugated, "ring rolled", or pleated. The process of "ring rolling" is described in U.S. Pat. No. 4,517,714 issued to Sneed. All of these treatments have to be carried out in the transverse direction to render the support web longitudinally expandable.

Generally, a deactivatable expansion obstruction means suitable for the present invention holds the delimiting transverse edges of a support web region comprising a longitudinal expansion means at a distance smaller than the longitudinal surface contour length between the two delimiting transverse edges, i.e. it obstructs a longitudinal expansion means from being fully expanded by web tensions insufficient to deactivate the deactivatable expansion obstruction means.

Deactivatable expansion obstruction means suitable for the present invention include but are not limited to adhesive bonding, ultrasonic bonding, heat bonding, pressure bonding, friction bonding, autogenous bonding or combinations of different bonding methods.

Another suitable deactivatable expansion obstruction means is a mechanical fixation by a mechanical fixation device such as a bracket, a thread or by fiber entanglement.

In case the continuous structure is made offline and supplied in continuous form to the process of the present invention, the combination with the support web may be achieved by means of combining rolls. In case the continuous structure is formed online, the forming may happen directly on the support web or the forming is carried out on a separate device such as a drum and the continuous structure is subsequently transferred onto the support web.

In case the continuous structure comprises designated separation zones, it is necessary to phase the continuous structure relative to the support web before combining the two such that the designated separation zones are adjacent to the longitudinal expansion means of the support web.

In order to maintain the combination of the continuous structure with the support web at a sufficiently constant phasing relative to each other, the two must have surfaces in contact with each other exhibiting a certain amount of friction such as by contacting surfaces having a certain roughness or by certain parts penetrating from one surface into the other (such as fiber entanglement). The friction between continuous structure and support web may also be enhanced by applying a vacuum to the outer side of either component, thereby sucking the other component towards the contacting surface of the first component.

To further reduce slippage of the continuous structure relative to the support web the continuous structure may also be joined to the support web. For this purpose, a wide variety of bonding techniques well known in the art may be used, such as adhesive bonding, ultrasonic bonding, or the like. Preferably, the continuous structure is joined only to those sections of the support web which do not comprise a longitudinal expansion means in order to only obstruct the subsequent longitudinal expansion of the support web to a lesser extent.

If the support web comprises deactivatable expansion obstruction means, they are preferably deactivated before the subsequent longitudinal expansion of the support web. Hereby, the specific type of deactivation depends on the type of the deactivatable expansion obstruction means comprised in the support web. Possible deactivation devices include a cutting device, an electromagnetic radiation emitting device, a heating device, a web tensioning device, a deactivation agent dispensing device, and the like.

In case the deactivatable expansion obstruction means are deactivatable by increased web tension, the deactivatable expansion obstruction means may alternatively be deactivated by the increased web tension imposed on the support web during the step of longitudinal expansion of the support web. One possible embodiment of a support web which allows this particular type of deactivation is a discontinuously expandable support web.

Optionally, the process of the present invention may comprise a step of introducing designated separation zones into the continuous structure. This may be achieved by at least partial separation of the elements comprised in the continuous web at the position adjacent to the longitudinal expansion means of the support web. Such partial separation of the elements may be achieved by local basis weight reduction, side notches, partial cutting, or the like. By this incorporation of designated separation zones into the continuous web of absorbent cores, the control over the formation of the separation edge of two neighboring absorbent cores may be enhanced. A means to achieve the at least partial separation of the absorbent cores may be a cutting device, trimming device, scarfing device, or the like.

After the step of combining the continuous structure and the support web and after preparing the continuous structure (if applicable), the support web is longitudinally expanded at the position of the longitudinal expansion means, thereby spacing apart the discrete elements. The spacing between the elements accordingly occurs at those positions which are adjacent to the longitudinal expansion means of the support web. In case the separation of the continuous structure into discrete elements had not been completed by any of the preceding steps, the complete separation is achieved during this step by simply pulling the designated elements apart by means of expanding the support web.

For the process step of expanding the support web, it is essential that the tension needed to separate the continuous structure into discrete elements is smaller than the tearing tension of the support web. Additionally, the separation tension of the continuous structure must be small enough to not cause substantial slippage of the continuous web relative to the support web.

The step of separating the continuous structure into discrete elements is followed by further expansion of the support web such that the discrete elements are longitudinally spaced apart.

In one embodiment of the present invention the longitudinal expansion of the support web is achieved by two consecutive conveyors transporting said support web, whereby the second conveyor has a higher speed that the first one. The speed difference imposes a longitudinal stress onto the support web which in turn expands at the positions of at least some of the longitudinal expansion means. The conveyors preferably comprise a means to reduce slippage of the support web relative to the conveyor belt during transport. Preferably, the friction of the support web on the conveyor belt is higher than the combined expansion tension of the support web (with deactivated expansion obstruction means and unexpanded longitudinal expansion means) and the expansion tension of the web material and is lower than the tearing tension of the support web (with fully expanded longitudinal expansion means). With this setup, tearing of the support web caused by a second conveyor which is running too fast can be avoided. One possible embodiment of the slippage reduction means is a vacuum that is applied to an apertured conveyor belt which sucks the support web onto the belt.

Another aspect of the present invention is a process to make discrete articles comprising at least one of the aforementioned discrete elements and at least one piece of support web. This process comprises the steps of the process of converting a continuous structure into discrete, spaced apart elements described in the present description and in addition comprises the step of subsequently separating the support web between at least some neighboring elements in order to obtain discrete articles.

In addition, the support web may be folded around at least one longitudinal or transverse edge of the discrete elements. Optionally, the support web is wrapped around the longitudinal edges of the discrete elements such that the longitudinal edges of the support web overlap. Furthermore, the wrapped around support web may be adhered to itself such that the absorbent cores are completely enveloped by the support web. For this purpose, the support web needs to be sealed along the overlapping longitudinal edges of the support web and outside the transverse edges of the discrete elements. For adhering the support web to itself, a wide variety of bonding techniques well known in the art may be used, such as adhesive bonding, heat bonding, ultrasonic bonding, or the like. Preferably, the material of the support web is designed such that most of the constituents of the discrete elements (such as particles, fibers, or the like) are unable to escape from the absorbent core through the support web.

In another embodiment of the process of the present invention, the support web combined with the discrete, spaced apart elements is brought together with a second support web, which can be the same, similar, or different. The discrete elements are positioned intermediate the support web and the second support web. Preferably, support web and second support web are continuously joined to each other outside the longitudinal and transverse edges of the absorbent core, thereby enveloping the absorbent core. For adhering the support web to the second support web, a wide variety of bonding techniques well known in the art may be used, such as adhesive bonding, heat bonding, ultrasonic bonding, or the like. Preferably, the material of the support web and the second support web are designed such that most of the constituents of the discrete elements (such as particles, fibers, or the like) are unable to escape from the element through either support web.

The process of the present invention is particularly well suited for the manufacture of disposable absorbent articles comprising at least one absorbent core.

The term "absorbent core", as used herein, refers to devices which are capable of handling liquids, such as accepting, distributing and retaining liquids, especially aqueous liquids and body exudates, e.g. urine, and more specifically refers to devices which are deployed in absorbent articles to handle liquids, especially aqueous liquids and body exudates, e.g. urine. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner.

Typically, an absorbent article comprises an absorbent core. The absorbent cores may comprise any absorbent material which is generally compressible, conformable, non-irritating to the wearer's skin, and capable of absorbing and retaining liquids such as urine and other certain body exudates. The absorbent cores may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue; absorbent foams; absorbent sponges; superabsorbent polymers; absorbent gelling materials; or any other known absorbent material or combinations of materials.

The configuration and construction of the absorbent core may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core should be compatible with the design loading and the intended use of the diaper 20. Exemplary absorbent structures for use as the absorbent cores are described in U.S. Pat. No. 4,610,678; U.S. Pat. No. 4,673,402; U.S. Pat. No. 4,834,735; U.S. Pat. No. 4,888,231; U.S. Pat. No. 5,147,345; and U.S. Pat. No. 5,342,338.

Suitable continuous structures of absorbent cores can be made online such as by airlaying a fibrous matrix along with other optional components of the absorbent core. It is also possible to pre-make suitable continuous structures of absorbent cores and subsequently to supply them to the process in continuous form such as roll stock.

After spacing apart the absorbent cores using the process of the present invention, the support web combined with the discrete cores may be brought together with a backsheet and a topsheet such that absorbent cores and support web are sandwiched between backsheet and topsheet. Hereby, the topsheet may be joined to the absorbent core side of the support web or to the opposite side. Accordingly, the backsheet is joined to that side of the support web which is opposite the topsheet. Preferably, topsheet and backsheet are joined to each other at least along their periphery to envelope the absorbent core. However, it is to be understood, that the support web carrying the discrete absorbent cores may also be combined with a topsheet only or a backsheet only. In this case, the absorbent cores are preferably sandwiched between the support web and topsheet or the backsheet respectively.

The backsheet is generally that portion of the diaper which prevents the exudates absorbed and contained therein from soiling articles which may contact the diaper, such as bed sheets and undergarments. In preferred embodiments, the backsheet is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper while still preventing exudates from passing through the backsheet. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096.

The topsheet is preferably compliant, soft feeling, and non-irritating to the wearer's skin. Further, at least a portion of the topsheet is liquid pervious, permitting liquids to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wetlaid, meltblown, hydroentangled, or otherwise processed as is known in the art. One suitable topsheet comprising a web of staple length polypropylene fibers is manufactured by Veratec, Inc., a Division of International Paper Company, of Walpole, Mass. under the designation P-8. Suitable formed film topsheets are described in U.S. Pat. No. 3,929,135; U.S. Pat. No. 4,342,314; U.S. Pat. No. 4,463,045; U.S. Pat. No. 5,006,394; U.S. Pat. No. 4,609,518; and U.S. Pat. No. 4,629,643.

Preferably, the topsheet is made of a hydrophobic material or is treated to be hydrophobic in order to isolate the wearer's skin from liquids contained in the absorbent core. If the topsheet is made of a hydrophobic material, preferably at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant or by incorporating a surfactant into the topsheet. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 and U.S. Pat. No. 4,988,345.

Alternatively, a topsheet made from hydrophobic materials may comprise apertures of at least 0.1 mm$^2$ which allow the penetration of body fluids into the hydrophobic absorbent core beneath the topsheet. Preferably, the topsheet is joined to the absorbent core underneath by means of a hydrophilic adhesive.

The backsheet web and the topsheet web and the spaced apart absorbent cores on the support web are brought into contact with one another at combining rolls. Just prior to the webs and the cores/support web coming into contact with one another (preferably after the longitudinal expansion means of the support web are fully expanded), additional adhesive is preferably applied to at least one of the webs. The latter adhesive secures predetermined portions of the backsheet, topsheet and absorbent core to one another to form the diaper web.

Finally, the diaper web is cut at predetermined locations along its length by means of knife to produce single use diapers.

In case the absorbent cores are positioned intermediate the support web and the backsheet, the support web may also be continuously joined to the backsheet along the longitudinal and transverse edges of the absorbent cores. Preferably, the material of the support web and the backsheet web are designed such that most of the elements of the absorbent core (such as particles of superabsorbent polymer, fibers, or the like) is unable to escape from the absorbent core through either the support web or the backsheet.

Additionally, the process of the present invention may comprise further steps such as attaching closure elements or elastification devices to the absorbent articles.

TEST METHODS

Elastic Modulus Test

The Elastic Modulus Test is used for measuring the elastic modulus which is defined as the slope of the expansion tension vs. relative elongation curve at 0% relative elongation. The tests are performed on an standard stress-strain analysis apparatus such as a Zwick Model 1445, available from Zwick GmbH & Co. of Ulm, Germany, which is interfaced to a Compaq Prolinea 466 computer available from Compaq Computer Corporation of Houston/Tex., USA, using Zwick 7047.4b software which is available from Zwick GmbH & Co. of Ulm, Germany. All essential parameters needed for testing are input in the software for each test. Also, all data collection, data analysis and graphing are done using the software.

The samples used for this test are 25.4 millimeters wide by 140 millimeters long with the long axis of the sample cut parallel to the longitudinal dimension of the web material. The sample should be cut with a sharp die cutter or some suitably sharp cutting device designed to cut a (25.4+/−1) millimeter wide sample. The sample should be cut so that an area representative of the symmetry of the of the longitudinal expansion means is represented. There will be cases (due to variations in either the size or distance of the longitudinal expansion means) in which it will be necessary to cut either larger or smaller samples than is suggested herein. In this case, it is very important to note (along with any data reported) the size of the sample, which area of the web material it was taken from and preferably include a schematic of the representative area used for the sample. Three samples of a given material are tested.

The grips of the apparatus consist of air actuated grips designed to concentrate the entire gripping force along a single line perpendicular to the direction of testing stress having one flat surface and an opposing face from which protrudes a half round to minimize slippage of the sample. The distance between the lines of gripping force should be 100 millimeters as measured by a steel rule held beside the grips. This distance will be referred to from hereon as the "gauge length". The sample is mounted in the grips with its long axis perpendicular to the direction of applied percent elongation. The crosshead speed is set to 500 millimeter per minute. The crosshead elongates the sample until the sample breaks at which point the crosshead stops and returns to its original position (0% elongation).

The elastic modulus measured by the apparatus for the three samples are averaged to obtain the final result.

Deactivatable Expansion Obstruction Test

The Deactivatable Expansion Obstruction Test is used to measure the Relative Elastic Modulus Reduction of a web material.

First, six identical samples of the web material, called A1, A2, A3, B1, B2, and B3 hereafter, are prepared following the instructions given in the Elastic Modulus Test. Each sample should comprise at least one longitudinal expansion means and at least one deactivatable expansion obstruction means. In case the sample size of the Elastic Modulus Test is sufficient to fulfill this requirement, the Elastic Modulus Test has to be modified to accommodate sufficiently large web material samples.

The samples A1, A2, and A3 are submitted to the Elastic Modulus Test. The resulting elastic moduli are averaged to obtain the elastic modulus EMA of the samples A1, A2, and A3. Then, the deactivatable expansion obstruction means comprised in the samples B1, B2, and B3 are deactivated and the modified samples are submitted to the Elastic Modulus Test. The resulting elastic moduli are averaged to obtain the elastic modulus EMB of the samples B1, B2, and B3.

Finally, the Relative Elastic Modulus Reduction is computed according to the formula (EMA−EMB)/EMA.

Expansion Tension Test

The Expansion Tension Test is used for measuring expansion tension versus percent elongation properties. The tests are performed on a standard stress strain curve measuring apparatus such as a Zwick Model 1445, available from Zwick GmbH & Co. of Ulm, Germany, which is interfaced to a Compaq Prolinea 466 computer available from Compaq Computer Corporation of Houston, Tex./USA, using Zwick 7047.4b software which is available from Zwick GmbH & Co. of Ulm, Germany. All essential parameters needed for testing are input in the Zwick 7047.4b software for each test. Also, all data collection, data analysis and graphing are done using the Zwick 7047.4b software.

The samples used for this test are 25.4 millimeters wide by 140 millimeters long with the long axis of the sample cut parallel to the longitudinal dimension of the web material. The sample should be cut with a sharp die cutter or some suitably sharp cutting device designed to cut a (25.4+/−1) millimeter wide sample without damaging the edges of the sample. The sample should be cut so that an area representative of the symmetry of the of the longitudinal expansion means is represented. There will be cases (due to variations in either the size or distance of the longitudinal expansion means) in which it will be necessary to cut either larger or smaller samples than is suggested herein. In this case, it is very important to note (along with any data reported) the size of the sample, which area of the web material it was taken from and preferably include a schematic of the representative area used for the sample. Three samples of a given material are tested.

The grips of the Zwick consist of air actuated grips designed to concentrate the entire gripping force along a single line perpendicular to the direction of testing stress having one flat surface and an opposing face from which protrudes a half round to minimize slippage of the sample. The distance between the lines of gripping force should be 100 millimeters as measured by a steel rule held beside the grips. This distance will be referred to from hereon as the "gauge length". The sample is mounted in the grips with its long axis perpendicular to the direction of applied percent elongation. The crosshead speed is set to 500 millimeter per minute. The crosshead elongates the sample until the sample breaks.

The result is a curve of the expansion tension as a function of the relative elongation of the web material is obtained.

Discontinuous Expansion Test

The Discontinuous Expansion Test is used to determine the Discontinuous Expansion Threshold, the Tearing Point, and the Relative Expansion Tension Reduction of a web material.

First, three identical samples of the web material, called samples A1, A2, and A3 hereafter, are submitted to the Expansion Tension Test.

From the resulting expansion tension vs. relative elongation curve for sample A1, the local maxima of the expansion are obtained together with the respective relative elongations (The submitted web material is not discontinuously expandable according to the present invention if the expansion tension vs. relative elongation curve comprises only one maximum). The local maximum having the smallest elongation is called Discontinuous Expansion Threshold with a respective expansion tension of T1 and a respective relative elongation E1. The local maximum having the largest elongation is called Tearing Point with a respective expansion tension T2 and a respective relative expansion E2. Now, the absolute expansion tension minimum intermediate E1 and E2 is obtained from the expansion tension vs. relative elongation curve of the web material. This minimum is called Discontinuous Expansion Point having a respective expansion tension T3, and a respective relative elongation E3. The same procedure is carried out for samples A2 and A3.

Finally, the expansion tensions T2 and T3 for the three samples are averaged and the Relative Expansion Tension Reduction RETR of the submitted web material is obtained via the formula RETR=(T2A−T3A)/T2A where T2A and T3A are the respective averages of T2 and T3.

While the test methods described above are useful for many of the web materials suitable as support webs for the process of the present invention it is recognized that the test method may have to be modified to accommodate some of the more complex web materials which are also suitable as a support web for the process of the present invention.

What is claimed is:

1. A process for converting a continuous structure into discrete, spaced apart elements, comprising the steps of:
    a) supplying a continuous support web which is combined with said continuous structure, said support web comprising at least one longitudinal expansion means;
    b) separating said continuous structure into said discrete elements by longitudinally expanding said continuous support web at said longitudinal expansion means; and
    c) longitudinally spacing apart said discrete elements by longitudinally expanding said continuous support web at said longitudinal expansion means.

2. The process according to claim 1 wherein said support web has at least one deactivatable expansion obstruction means preventing the longitudinal expansion means from being fully expanded prior to the deactivatable expansion obstruction means being deactivated.

3. The process according to claim 2 further comprising the step of deactivating said deactivatable expansion obstruction means.

4. The process according to claim 1 wherein said support web is a discontinuously expanding web.

5. The process according to claim 1 further comprising the step of introducing designated transverse separation zones into the continuous structure.

6. The process according to claim 1 wherein said expanding of said support web is carried out by a series of two consecutive conveyors transporting said support web, a second of the two conveyors having a higher transportation velocity than a first of the two conveyors.

7. The process according to claim 1 further comprising the steps of forming said continuous structure and transferring said continuous structure onto said support web.

8. The process according to claim 1 further comprising the step of forming said continuous structure on said support web.

9. The process according to claim 1 wherein said discrete elements are absorbent cores.

10. The process according to claim 1 further comprising the step of separating said continuous support web between at least some said discrete elements to thereby form discrete articles comprising at least one of said discrete elements and at least one piece of said support web.

11. The process according to claim 10 further comprising the step of folding said support web around at least one longitudinal edge or at least one transverse edge of said discrete elements.

12. The process according to claim 11 further comprising the steps of longitudinally wrapping said support web around said discrete elements such that the longitudinal edges of said support web overlap and completely enveloping said discrete elements by sealing said support web along the overlapping longitudinal edges of said support web and by sealing said support web outside the transverse edges of said discrete elements.

13. The process according to claim 10 further comprising the steps of supplying a second support web and positioning said discrete elements intermediate said support web and said second support web.

14. The process according to claim 13 further comprising the step of completely enveloping said discrete elements by attaching said support web to said second support web outside the longitudinal edges and transverse edges of said discrete elements.

15. The process according to claim 10 wherein said discrete articles are absorbent articles.

* * * * *